(12) United States Patent
Irie

(10) Patent No.: US 9,050,052 B2
(45) Date of Patent: Jun. 9, 2015

(54) ULTRASOUND ENDOSCOPE

(71) Applicant: OLYMPUS MEDICAL SYSTEMS CORP., Tokyo (JP)

(72) Inventor: Kei Irie, Akiruno (JP)

(73) Assignee: OLYMPUS MEDICAL SYSTEMS CORP., Tokyo (JP)

(*) Notice: Subject to any disclaimer, the term of this patent is extended or adjusted under 35 U.S.C. 154(b) by 0 days.

(21) Appl. No.: 13/965,414

(22) Filed: Aug. 13, 2013

(65) Prior Publication Data

US 2014/0058269 A1    Feb. 27, 2014

Related U.S. Application Data

(63) Continuation of application No. PCT/JP2013/063807, filed on May 17, 2013.

(30) Foreign Application Priority Data

Aug. 27, 2012    (JP) .................................. 2012-186871

(51) Int. Cl.
*A61B 8/14*    (2006.01)
*A61B 8/00*    (2006.01)
*A61B 8/12*    (2006.01)

(52) U.S. Cl.
CPC ................. *A61B 8/4444* (2013.01); *A61B 8/12* (2013.01); *A61B 8/445* (2013.01)

(58) Field of Classification Search
None
See application file for complete search history.

(56) References Cited

U.S. PATENT DOCUMENTS

| | | | |
|---|---|---|---|
| 4,605,009 A | 8/1986 | Pourcelot et al. | |
| 5,467,779 A * | 11/1995 | Smith et al. ................... | 600/445 |
| 2006/0058676 A1 | 3/2006 | Yagi et al. | |
| 2008/0084137 A1 | 4/2008 | Wakabayashi et al. | |
| 2009/0093725 A1 | 4/2009 | Sato et al. | |
| 2011/0166455 A1 | 7/2011 | Cully et al. | |

FOREIGN PATENT DOCUMENTS

| | | |
|---|---|---|
| JP | 01-291846 A | 11/1989 |
| JP | H02-271843 A | 11/1990 |
| JP | 05-015536 A | 1/1993 |
| JP | H06-335481 A | 12/1994 |
| JP | 2003-033354 A | 2/2003 |
| JP | 2004-209044 A | 7/2004 |
| JP | 2005-218519 A | 8/2005 |
| WO | WO 03/086196 A1 | 10/2003 |

OTHER PUBLICATIONS

Extended Supplementary European Search Report dated Mar. 16, 2015 from related European Application No. 13 79 5683.5.

* cited by examiner

*Primary Examiner* — Unsu Jung
*Assistant Examiner* — Michael N Fisher
(74) *Attorney, Agent, or Firm* — Scully, Scott, Murphy & Presser, P.C.

(57) ABSTRACT

A wiring board electrically connected to a back side of an ultrasound transmitting/receiving section that transmits/receives ultrasound includes a rigid circuit board included in a stiff portion, and a wrapping portion extending out from the rigid circuit board (stiff portion), and a plurality of drive wirings electrically connected to the wiring board are inserted into a wiring insertion portion of a housing with the plurality of drive wirings wrapped and bundled by the wrapping portion.

8 Claims, 12 Drawing Sheets

ULTRASOUND ENDOSCOPE

CROSS REFERENCE TO RELATED APPLICATION

This application is a continuation application of PCT/JP2013/063807 filed on May 17, 2013 and claims benefit of Japanese Application No. 2012-186871 filed in Japan on Aug. 27, 2012, the entire contents of which are incorporated herein by this reference.

BACKGROUND OF THE INVENTION

1. Field of the Invention

The present invention relates to an ultrasound endoscope with a transducer unit housed in a housing provided in a distal end portion of an insertion portion.

2. Description of the Related Art

Conventionally, in, e.g., medical fields, ultrasound endoscopes including an ultrasound probe at a distal end of an elongated insertion portion of an endoscope have widely been used. Each such ultrasound endoscope forms an ultrasound endoscope system jointly with, for example, an ultrasound observation apparatus and a monitor. The ultrasound endoscope system, for example, transmits ultrasound from an ultrasound probe to a subject and processes a received ultrasound echo signal in the ultrasound observation apparatus, enabling provision of an ultrasound tomographic image of an inside of the subject.

The ultrasound probe used in each such ultrasound endoscope includes, for example, a transducer unit resulting from unitization of a plurality of ultrasound transducers together with an acoustic matching layer and a back-side damping layer, and the transducer unit is housed in a housing portion formed in a housing, whereby a main part of the ultrasound probe is formed. Here, in the transducer unit, a wiring board electrically connected to the respective ultrasound transducers is provided, and a plurality of drive wirings separately extending from the cable unit so as to correspond to the respective ultrasound transducers are electrically connected to respective terminals on the wiring board, respectively. Also, in order to route the cable unit inside the insertion portion of the endoscope, a tubular wiring insertion portion (pipe portion) is provided so as to connect to the housing portion of the transducer unit formed in the housing (see, for example, Japanese Patent Application Laid-Open Publication No. 2004-209044). When such ultrasound probe is assembled, first, the work of inserting the proximal end side of the cable unit into the wiring insertion portion from the housing portion side and then pushing the group of drive wirings forking from a distal end portion of the cable unit into the wiring insertion portion and the work of housing the transducer unit in the housing portion of the housing are performed.

In such type of ultrasound endoscopes, there is a strong demand for downsizing of ultrasound probes, and examples of measures to respond to such demands may include reduction in distance from the transducer unit to a mouth of the wiring insertion portion and reduction in diameter of the wiring insertion portion.

SUMMARY OF THE INVENTION

An ultrasound endoscope according to an aspect of the present invention includes: an ultrasound transmitting/receiving section that transmits/receives ultrasound; at least one wiring board electrically connected to a back side of the ultrasound transmitting/receiving section; a plurality of drive wirings electrically connected to the wiring board; and a housing that houses the wiring board and holds the ultrasound transmitting/receiving section, wherein the housing includes a housing portion that houses the wiring board, and a tubular wiring insertion portion having a diameter smaller than the housing portion, the wiring insertion portion connecting to the housing portion; and wherein the wiring board includes a stiff portion electrically connected to the back side of the ultrasound transmitting/receiving section, a wrapping portion extending out from the stiff portion, the wrapping portion wrapping and bundling the plurality of the drive wirings and being inserted into the wiring insertion portion, and a protection sheet that extends out from the stiff portion and covers a portion of connection with the plurality of drive wirings.

DETAILED DESCRIPTION OF THE PREFERRED EMBODIMENT

Figure 1:
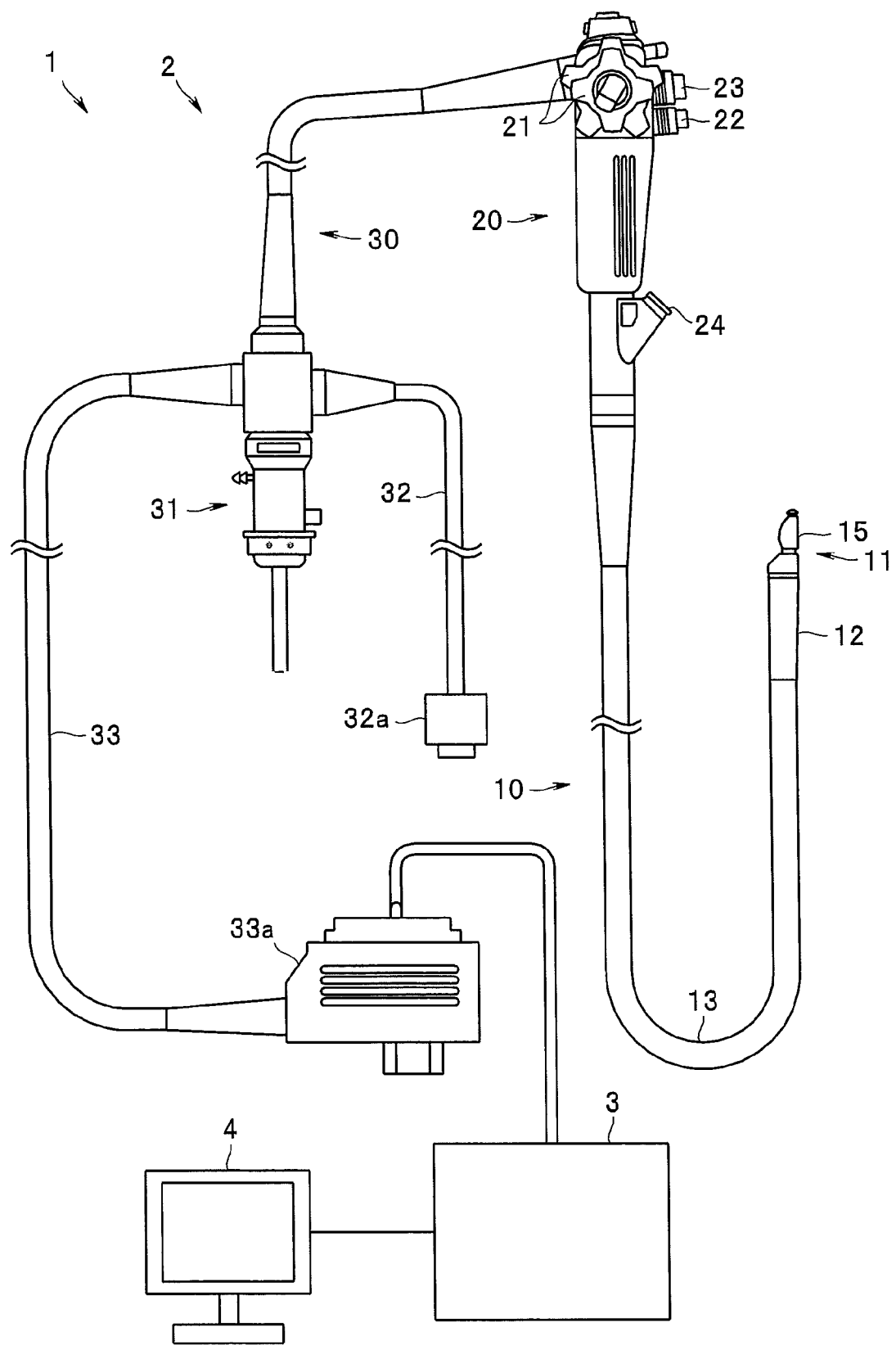
FIG. 1 is a diagram of a schematic configuration of an ultrasound endoscope.
Figure 2:
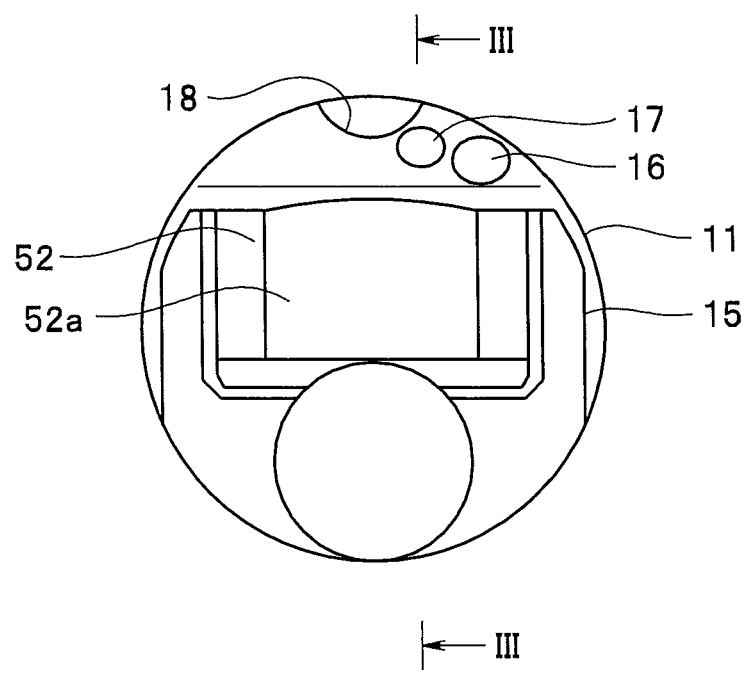
FIG. 2 is a diagram of an end face of a distal end rigid portion.
Figure 3:
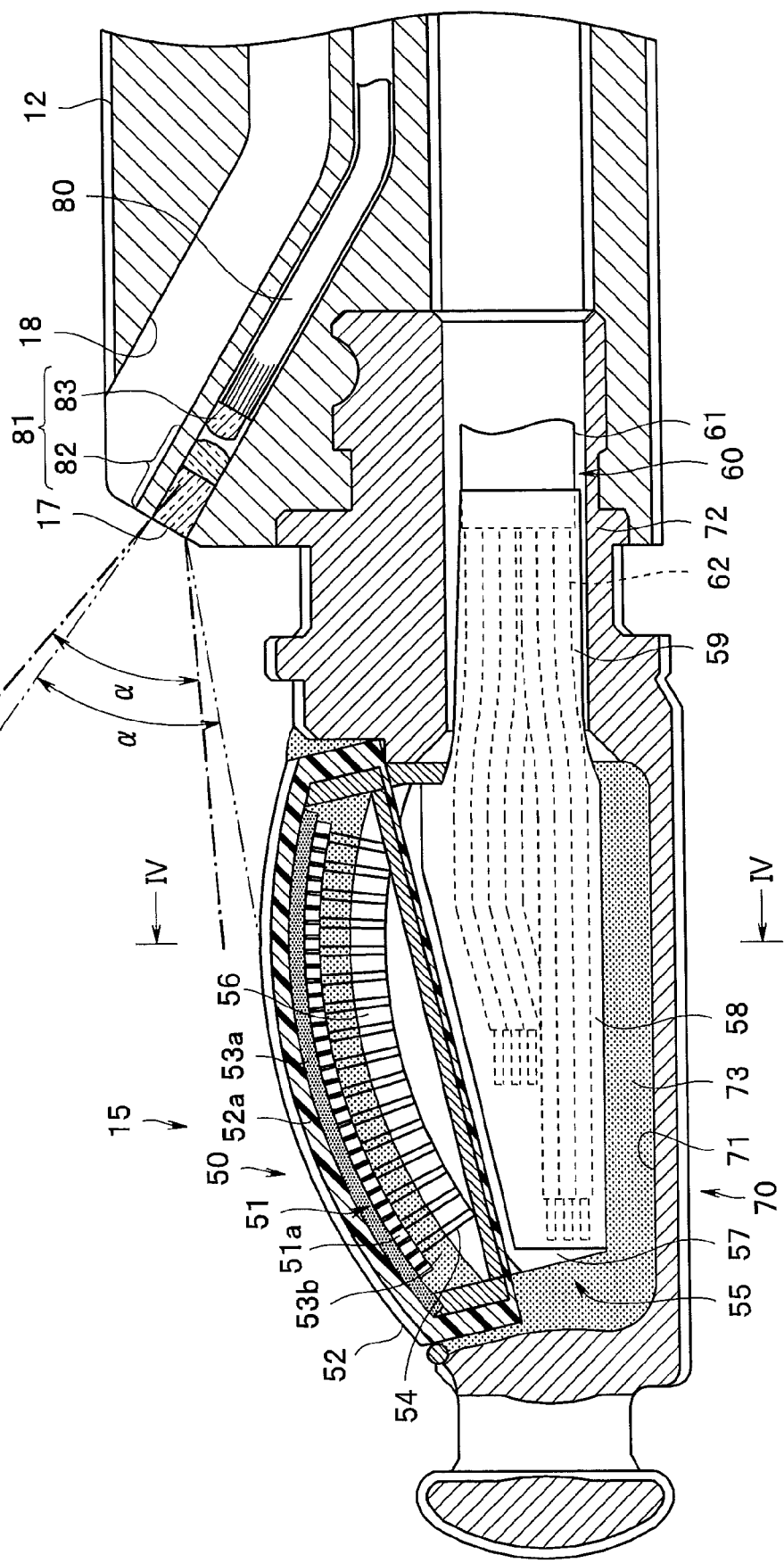
FIG. 3 is a cross-sectional view along line III-III in FIG. 2.
Figure 4:
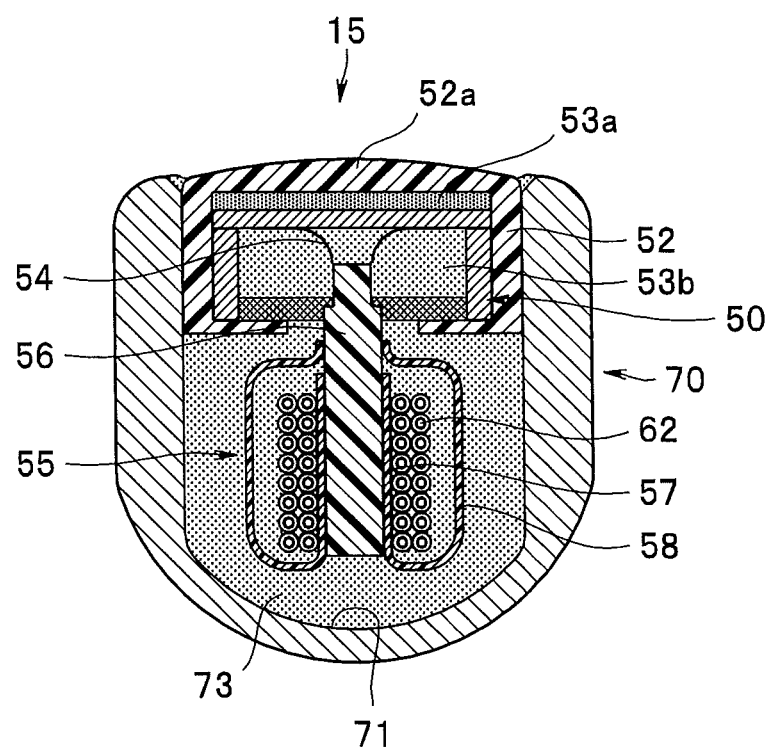
FIG. 4 is a cross-sectional view along line IV-IV in FIG. 3.
Figure 5:
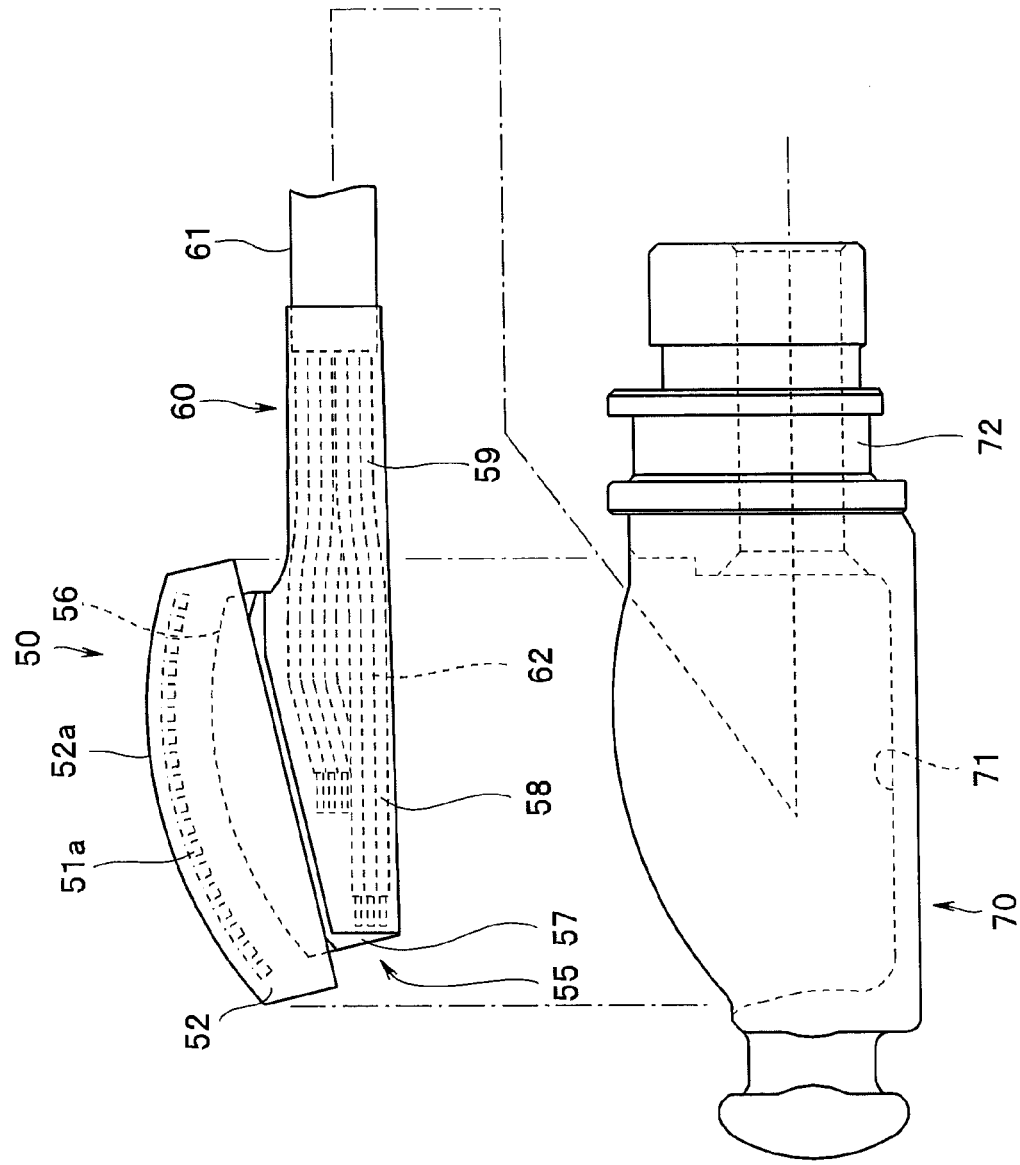
FIG. 5 is an exploded side view illustrating a transducer unit to which a cable unit is connected, and a housing.
Figure 6:
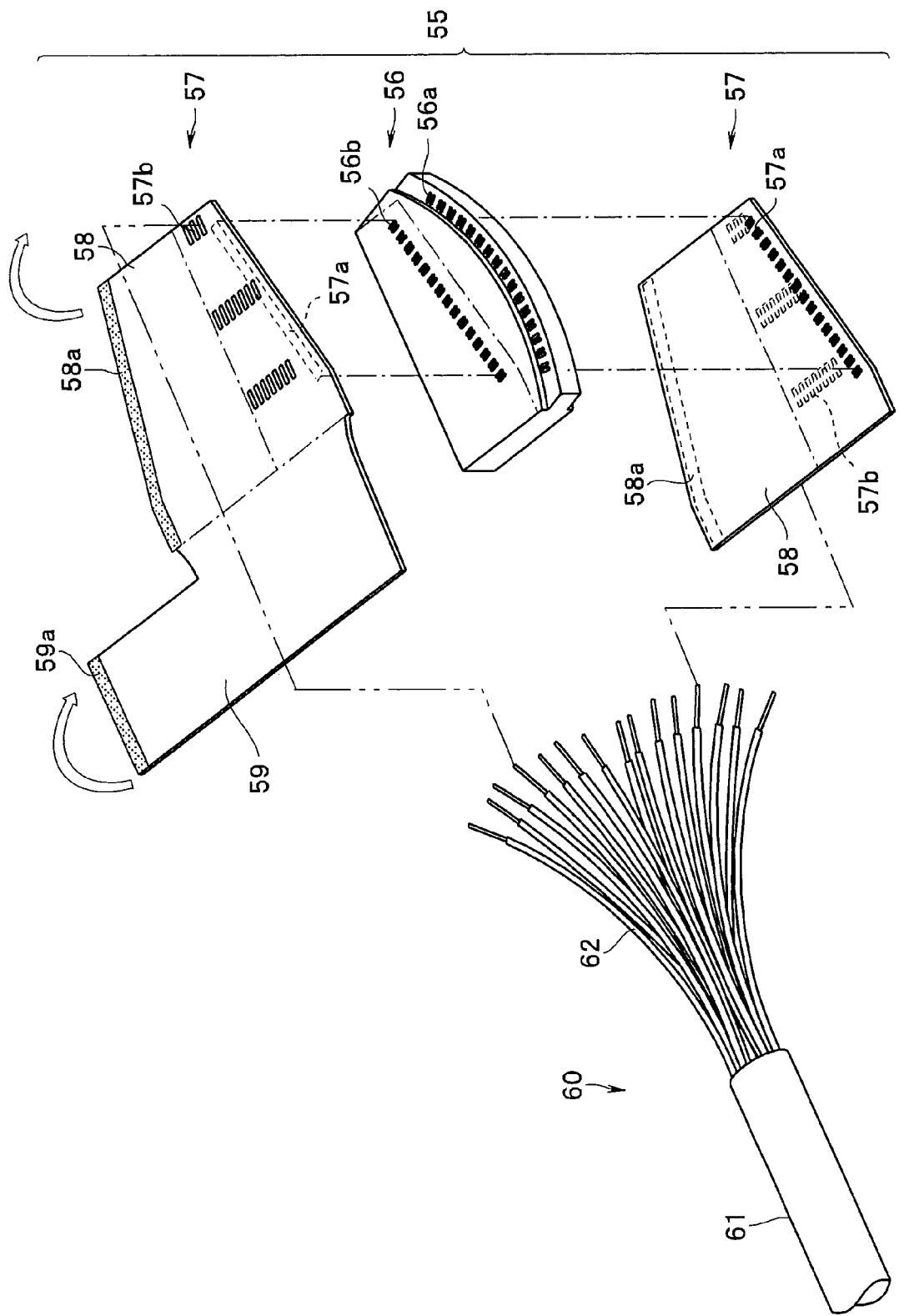
FIG. 6 is an exploded perspective view illustrating a wiring board and a cable unit.
Figure 7:
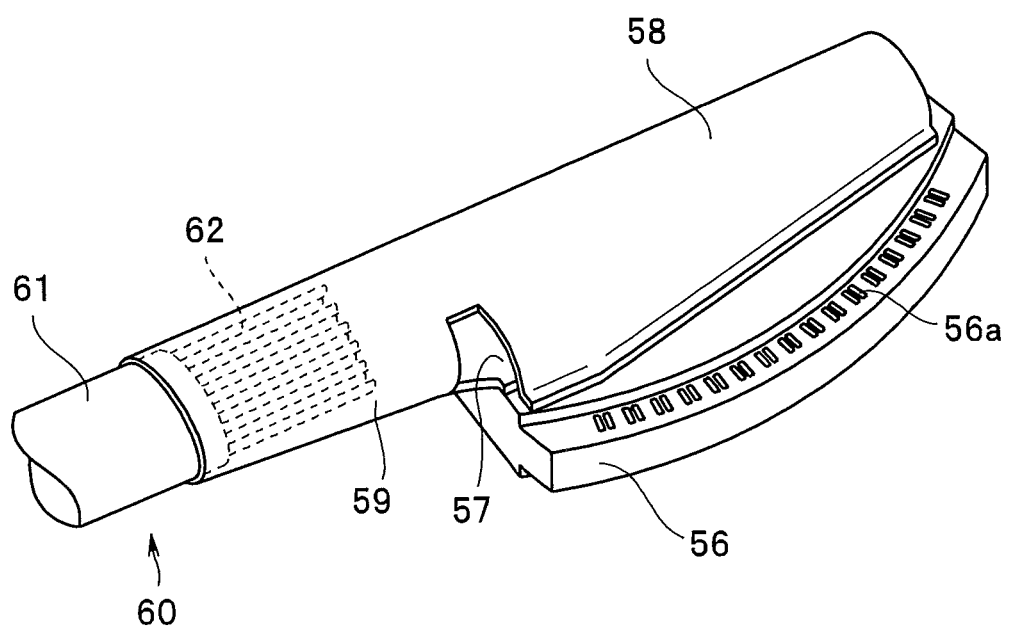
FIG. 7 is a perspective view of a wiring board to which a cable unit is connected.
Figure 8:
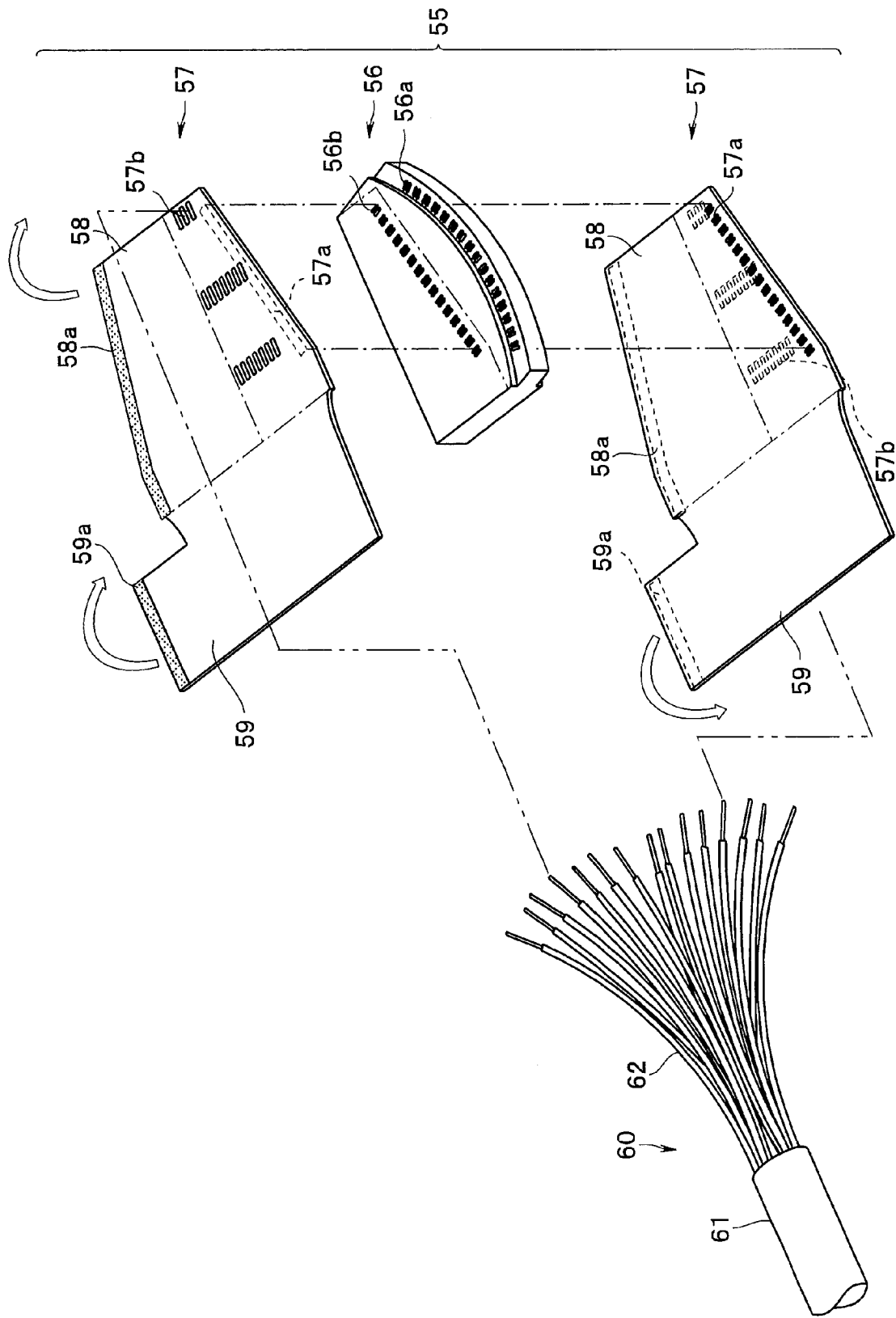
FIG. 8 is an exploded perspective view illustrating a modification of the wiring board and the cable unit.
Figure 9:
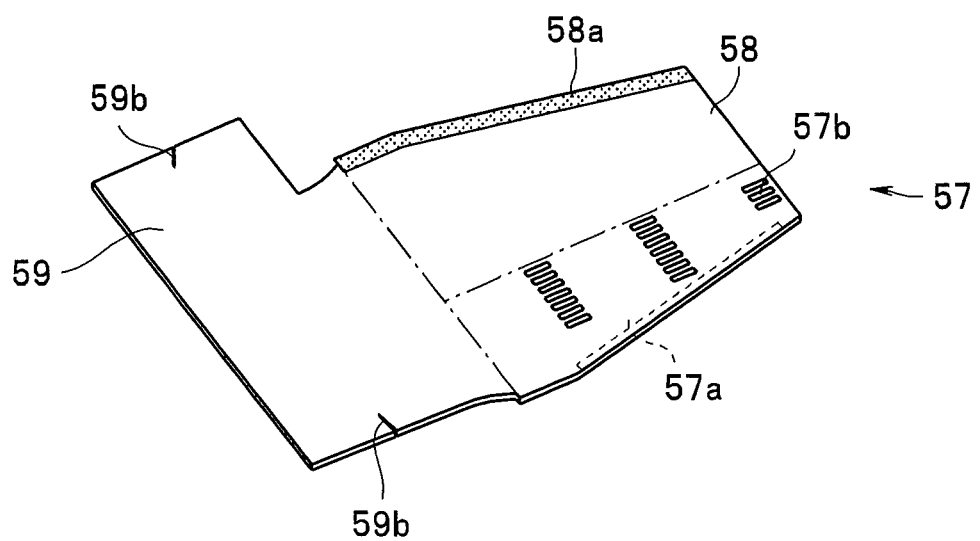
FIG. 9 is a perspective view illustrating a modification of a flexible sheet.

An embodiment of the present invention will be described below with reference to the drawings. The drawings relate to the embodiment of the present invention: FIG. 1 is a diagram of a schematic configuration of an ultrasound endoscope; FIG. 2 is a diagram of an end face of a distal end rigid portion; FIG. 3 is a cross-sectional view along line III-III in FIG. 2; FIG. 4 is a cross-sectional view along line IV-IV in FIG. 3; FIG. 5 is an exploded side view illustrating a transducer unit to which a cable unit is connected, and a housing; FIG. 6 is an exploded perspective view illustrating a wiring board and a cable unit; FIG. 7 is a perspective view of a wiring board to which a cable unit is connected; FIG. 8 is an exploded perspective view illustrating a modification of the wiring board and the cable unit; and FIG. 9 is a perspective view illustrating a modification of a flexible sheet.

An ultrasound endoscope system 1, which is illustrated in FIG. 1, includes an ultrasound endoscope 2, an ultrasound observation apparatus 3 and a monitor 4. Also, the ultrasound endoscope 2 includes an elongated insertion portion 10 to be inserted into a body, an operation section 20 provided so as to be continuous with a proximal end of the insertion portion 10, and a universal cord 30 extending from a side portion of the operation section 20.

Here, a connector 31 connected to a light source apparatus (not illustrated) is provided at a proximal end portion of the universal cord 30. A cable 32 connected to a camera control unit (not illustrated) via a connector 32a and a cable 33 detachably connected to the ultrasound observation apparatus 3 via a connector 33a extend out from the connector 31. The ultrasound observation apparatus 3 is connected to the ultrasound endoscope 2 via the connector 33a and the monitor 4 is connected to the ultrasound endoscope 2 via the ultrasound observation apparatus 3.

The insertion portion 10 includes a main part including a distal end rigid portion 11, a bending portion 12 positioned at a rear end of the distal end rigid portion 11, and a flexible tube portion 13 positioned at a rear end of the bending portion 12 and extending to the operation section 20, the tube portion 13 having a small diameter, a long length and flexibility, which are continuously provided in this order from the distal end side.

As illustrated in FIG. 2, an ultrasound probe 15 is disposed on the distal end side of the distal end rigid portion 11. Furthermore, in a slant surface formed at a part of the distal end rigid portion 11 on the proximal side relative to the ultrasound probe 15, an illumination lens 16 included in an illumination optical system, an observation lens 17 for an observation lens optical system, a forceps port 18 that doubles as a suction port and a non-illustrated air/water feeding nozzle are disposed.

At the operation section 20, an angle knob 21 for performing bending control to bend the bending portion 12 in a desired direction, an air/water feeding button 22 for performing air feeding and water feeding operations, a suction button 23 for performing an suction operation, and a treatment instrument insertion port 24, which is an entrance for a treatment instrument to be introduced into a body, are disposed. Here, the treatment instrument insertion port 24 connects to the forceps port 18 via a treatment instrument insertion channel (not illustrated) provided inside the insertion portion 10.

As illustrated in FIGS. 2 to 5, the ultrasound probe 15 in the present embodiment is a convex-type ultrasound probe, and the ultrasound probe 15 includes, for example, a transducer unit 50 that transmits/receives ultrasound, a cable unit 60 electrically connected to the transducer unit 50, and a housing 70 that holds the transducer unit 50.

The transducer unit 50 includes an ultrasound transmitting/receiving section 51 including a plurality of elongated ultrasound transducer elements 51a arranged in a substantially arc-like shape as a result of respective long sides of the ultrasound transducer elements 51a being jointed to one another. The ultrasound transmitting/receiving section 51 is housed in a protection cover 52 in which a substantially arc-like acoustic lens layer 52a is provided in an integrated manner. Inside the protection cover 52, the respective ultrasound transducer elements 51a are arranged so as to face an inner face of the acoustic lens layer 52a and are bonded to the inner face of the acoustic lens layer 52a via an acoustic matching layer 53a.

Also, inside the protection cover 52, an end portion of a wiring board 55 is made to face the back side of the respective ultrasound transducer elements 51a. On the end portion of the wiring board 55, electrode portions 56a, which correspond to the respective ultrasound transducer elements 51a, are provided, and the ultrasound transducer elements 51a are electrically and mechanically connected to the electrode portions 56a via wires 54. Note that for the connection of the wires 54, e.g., soldering is preferably used. Furthermore, inside the protection cover 52, for example, an adhesive having a predetermined elasticity or the like is charged, whereby a back-side damping layer (backing layer) 53b is formed, and the respective wires 54 are sealed by the back-side damping layer 53b.

Here, for example, as illustrated in FIG. 6, more specifically, the wiring board 55 includes a rigid circuit board 56, which is a stiff portion, and a pair of flexible circuit boards 57 attached to opposite faces of the rigid circuit board 56, respectively.

At each of the opposite faces of the rigid circuit board 56, a wiring pattern including the aforementioned respective electrode portions 56a and a plurality of pad electrodes 56b electrically connected to the respective electrode portions 56a are formed.

On one surface (inner side) of each flexible circuit board 57 that faces the rigid circuit board 56, a plurality of inner electrode portions 57a, which correspond to the pad electrodes 56b are arranged, and on the other surface (outer) side, a wring pattern in which a plurality of outer electrode portions 57b electrically connected to the respective inner electrode portions 57a, respectively, are arranged is formed. Furthermore, a protection sheet 58 extends out from each of the flexible circuit boards 57, the protection sheet 58 having a shape substantially symmetrical to the flexible circuit board 57. Furthermore, a strip-shaped wrapping portion 59 extends out from one of the flexible circuit boards 57. The protection sheet 58 and the wrapping portion 59 include, for example, a sheet material having flexibility and an insulating property, and are formed integrally with the flexible circuit board 57.

The inner sides of the respective flexible circuit boards 57 are bonded to the respective faces of the rigid circuit board 56. The bonding of the flexible circuit boards 57 are performed by, for example, bonding the flexible circuit boards 57 to the rigid circuit board 56 via thermal compression bonding or soldering with the respective inner electrode portions 57a on the flexible circuit board 57 positioned relative to the respective pad electrodes 56b on the rigid circuit board 56. As a result of bonding the flexible circuit boards 57 to the rigid circuit board 56, the respective inner electrode portions 57a on each of the flexible circuit boards 57 are electrically connected to the respective pad electrode 56b on the rigid circuit board 56. It is desirable that an adhesive used for the thermal compression bonding between the rigid circuit board 56 and the flexible circuit board 57 be a crosslinkable adhesive.

The cable unit 60 includes, for example, a wiring group resulting from a plurality of drive wirings 62, which each include a small-diameter coaxial cable, being integrally bundled by an outer coat 61. At a distal end portion of the cable unit 60, the respective drive wirings 62 extend out branchingly from the outer coat 61. Distal end portions of the respective separated drive wirings 62 are electrically connected to the respective outer electrode portions 57b, respectively, on the outer sides of the respective flexible circuit board 57. Through the connection with the respective outer electrode portions 57b, the respective drive wirings 62 are electrically connected to the respective ultrasound transducer elements 51a. Note that for the connection of the drive wirings 62, e.g., soldering is preferably used.

Here, after the respective drive wirings 62 in the cable unit 60 are electrically connected to the respective outer electrode portions 57b, the protection sheets 58 extending out from the respective flexible circuit boards 57 are folded back so as to cover the respective outer electrode portions 57*b*, and distal end portions of the protection sheets 58 are bonded to the rigid circuit board 56 via, for example, an adhesive 58*a* (see FIG. 4). Consequently, portions of connection between the respective outer electrode portions 57*b* and the respective drive wirings 62 are mechanically protected and electrically shielded.

Furthermore, the wrapping portion 59 extending out from one of the flexible circuit boards 57 is wound around peripheral portions of the respective drive wirings 62 exposed from the outer coat 61, and, for example, a distal end portion of the wrapping portion 59 is bonded to a part at a certain position of the wrapping portion 59 via an adhesive 59*a*. Consequently, the respective drive wirings 62 exposed from the outer coat 61 are integrally bundled by the wrapping portion 59 (see FIGS. 5 and 7), and the respective drive wirings 62 are mechanically protected and electrically shielded.

As illustrated in FIGS. 3 to 5, the housing 70 includes, for example, a member having a substantially U-shape in cross-section in which the housing portion 71 for the transducer unit 50 is provided in a recessed manner. On the proximal side of the housing 70, a tubular wiring insertion portion 72 having a function as a connector for connection with the distal end rigid portion 11 is provided, and the inside of the wiring insertion portion 72 connects to the inside of the housing portion 71.

Where the transducer unit 50 is assembled to such housing 70, for example, as illustrated in FIG. 5, first, the proximal end side of the cable unit 60 is inserted into and through the wiring insertion portion 72 from the housing portion 71 side. Subsequently, the insertion work of pushing the respective drive wirings 62 integrally bundled by the wrapping portion 59 into the wiring insertion portion 72 and the work of housing the transducer unit 50 in the housing portion 71 are performed. Note that after the transducer unit 50 is housed in the housing portion 71, and inside the housing portion 71, for example, a resin adhesive 73 is charged through the wiring insertion portion 72.

According to such embodiment as described above, the wiring board 55 electrically connected to the back side of the ultrasound transmitting/receiving section 51 that transmits/receives ultrasound includes the rigid circuit board 56, which provides a stiff portion, and the wrapping portion 59 extending out from the rigid circuit board 56 (stiff portion), and the plurality of the drive wirings 62 electrically connected to the wiring board 55 are inserted into the wiring insertion portion 72 of the housing 70 with the drive wirings 62 wrapped and bundled by the wrapping portion 59, enabling sufficient downsizing of the ultrasound probe 15 with a simple configuration and without losing the ease of assembly.

In other words, as a result of the plurality of drive wirings 62 being wrapped and bundled by the wrapping portion 59, direct interference between, e.g., a mouth of the wiring insertion portion 70 and the respective drive wirings 62 can be avoided when the respective drive wirings 62 are pushed into the wiring insertion portion 72. Accordingly, for example, when the ultrasound probe 15 is assembled, even if respective drive wirings 62 having an extremely small diameter are pressed to, e.g., the mouth of the wiring insertion portion 72 while the respective drive wirings 62 are bent at a relatively large curvature, e.g., mechanical damage of the respective drive wirings 62 can significantly be reduced. Accordingly, for example, reduction in distance from the transducer unit 50 to the mouth of the wiring insertion portion 72 and reduction in diameter of the wiring insertion portion 72 can easily be achieved, enabling sufficient downsizing of the ultrasound probe 15.

Here, in the configuration in which the respective drive wirings 62 are electrically connected to the rigid circuit board 56 via the flexible circuit boards 57, the wrapping portion 59 is formed integrally with the relevant flexible circuit board 57, enabling the wrapping portion 59 to extend out from the stiff portion (rigid circuit board 56) with a simpler configuration and without use of, e.g., a dedicated sheet material. In addition, as a result of the wrapping portion 59 being formed integrally with the relevant flexible circuit board 57 as described above, there is no need to provide, e.g., a space for bonding the proximal end side of the wrapping portion 59 onto the rigid circuit board 56, enabling downsizing of the wiring board 55 by that amount.

Furthermore, as a result of the protection sheet 58 for mechanically protecting and electrically insulating the portions of connection with the respective drive wirings 62 being made to extend out from each of the flexible circuit boards 57, there is no need to provide a space for bonding the proximal end side of the protection sheet 58 on the rigid circuit board 56, enabling downsizing of the wiring board 55 by that amount.

Although the above embodiment has been described in terms of an example of the configuration in which the wrapping portion 59 is provided at one of the pair of flexible circuit boards 57 and all of the respective drive wirings 62 connected to the respective flexible circuit boards 57 are integrally wrapped and bundled, as illustrated in FIG. 8, for example, a configuration in which a wrapping portion 59 is formed integrally with each of flexible circuit boards 57 and respective drive wirings 62 are wrapped and bundled by the respective flexible circuit boards 57 can be employed.

Furthermore, although the above embodiment has been described in terms of an example of the configuration in which the distal end portion of the wrapping portion 59 is bonded using the adhesive 59*a*, for example, an adhesive tape (not illustrated) or the like can be used instead of the adhesive 59*a*. Furthermore, for example, as illustrated in FIG. 9, a configuration in which slit portions 59*b* are provided in a wrapping portion 59 and a wound wrapping state of the wrapping portion 59 is maintained by engagement of the slit portions 59*b* can be employed.

In this type of ultrasound endoscope 2, when an optical image of the inside of a subject is observed, it is desirable to prevent the ultrasound probe 15 from appearing in the optical image. For that purpose, in an ultrasound endoscope 2, in general, an optical axis of an observation optical lens arranged in a distal end rigid portion 11 is arranged so as to be inclined upward relative to a longitudinal axis direction of the insertion portion 10 at a relatively sharp angle of around 35 to 55 degrees. However, in particular, in an ultrasound endoscope 2 employing an optical method in which an optical image is conveyed to the operation section 20 side using an image guide bundle 80, if such inclined angle is provided in a narrow distal end rigid portion 11, it is necessary to bend the image guide bundle 80 at a large curvature, resulting in a bending load on the bent region. On the other hand, setting a view angle of an obtained optical image to be small or setting a dimension in the longitudinal axis direction of the distal end rigid portion 11 to be large are not preferable from a practical perspective.

Figure 10:
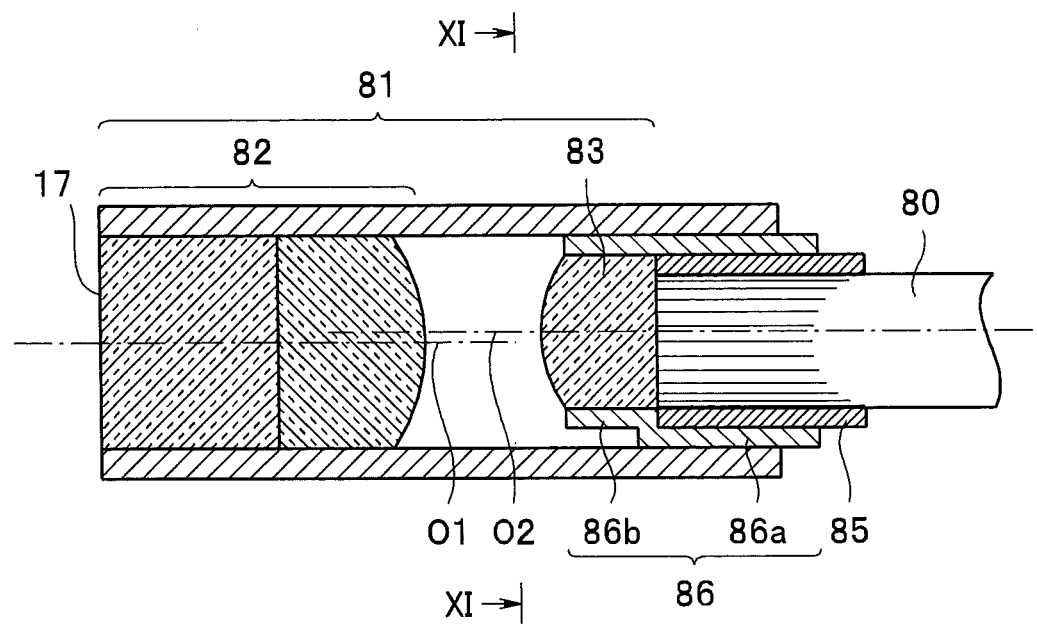
FIG. 10 is a cross-sectional view of a main part of an observation optical lens system.
Figure 11:
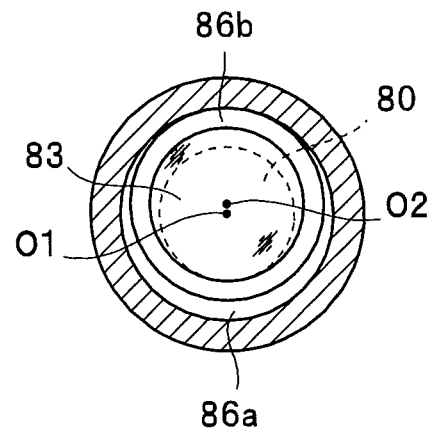
FIG. 11 is a cross-sectional view along line XI-XI in FIG. 10.

Therefore, in order to solve such problem, for example, in an observation optical lens system 81, which is illustrated in FIGS. 10 and 11, an optical axis O2 of an image guide bundle lens 83 fixed to a distal end portion of an image guide bundle 80 arranged so as to be offset from an optical axis O1 of an objective lens group 82 including an observation lens 17 in an upward side. In order to achieve such offset state, in a sleeve 85 provided at the distal end portion of the image guide bundle 80, a lens barrel 86 including a fitting portion 86a for the sleeve 85 and a lens holding portion 86b provided so as to be continuous with the fitting portion 86a, which are decentered, is fitted. As a result of the image guide bundle lens 83 being held via the lens barrel 86, for example, as illustrated in FIG. 3, even if the image guide bundle 80 is bent at a relatively small curvature, it is possible to prevent the ultrasound probe 15 from appearing on an optical image without setting an angle of view a to be small and setting the dimension in longitudinal axis direction of the distal end rigid portion 11 to be large (see the alternate long and short dash lines in FIG. 3). Note that in FIG. 3, the area indicated by the alternate long and two short dashes lines indicates an area that can be observed when the offset of the image guide bundle lens 83 is not performed as a comparative example.

Figure 12:
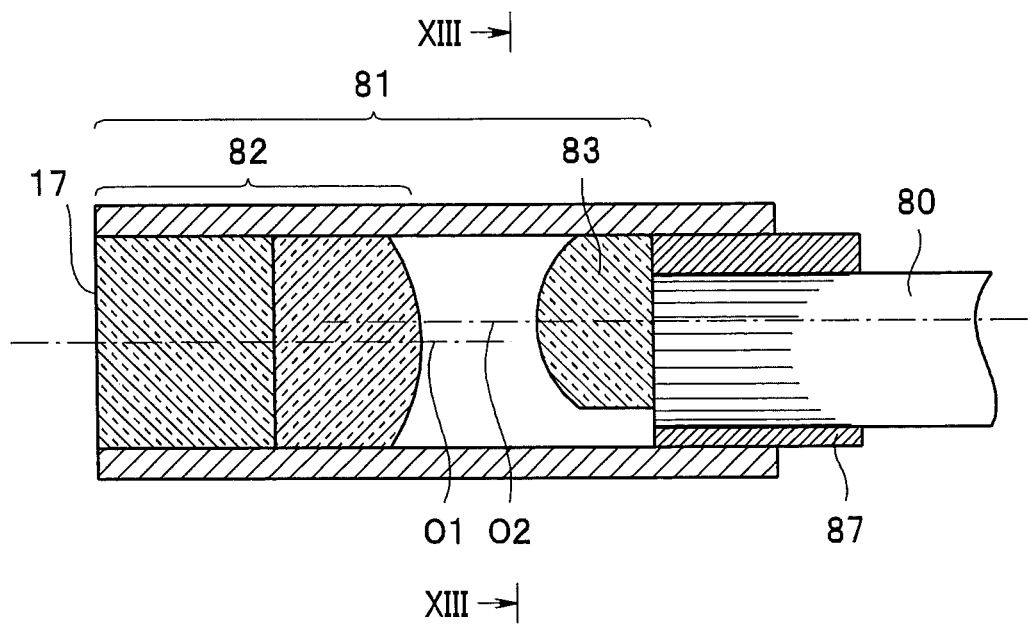
FIG. 12 is a cross-sectional view of a main part, which illustrates a modification of the observation optical lens system.
Figure 13:
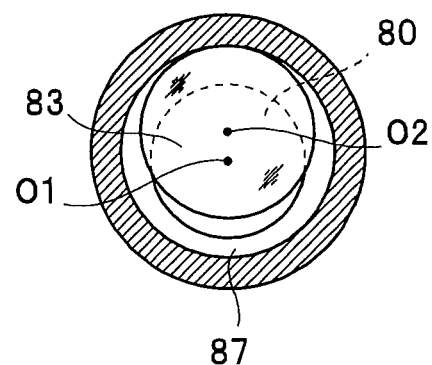
FIG. 13 is a cross-sectional view along line XIII-XIII in FIG. 12.
Figure 14:
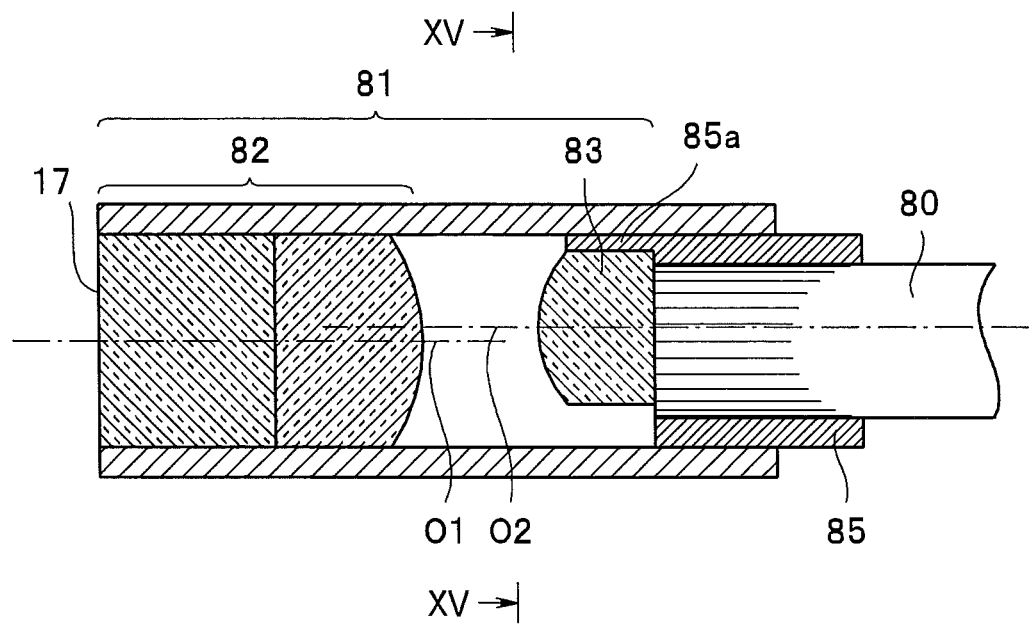
FIG. 14 is a cross-sectional view of a main part, which illustrates a modification of the observation optical lens system.
Figure 15:
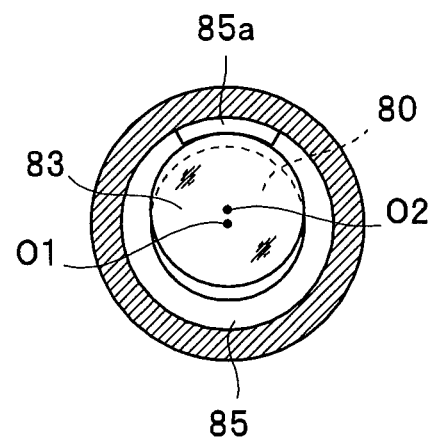
FIG. 15 is a cross-sectional view along XV-XV in line FIG. 14.

Here, for example, as illustrated in FIGS. 12 and 13, such positioning of an image guide bundle lens 83 can also be achieved with reference to an outer circumferential face of a sleeve 87 decentered by decentering a hole of a sleeve 87 that receives an image guide bundle 80. Furthermore, for example, as illustrated in FIGS. 14 and 15, the positioning of an image light guide bundle lens 83 can also be achieved with reference to a projection portion 85a for positioning, which is provided at a portion of a distal end portion of a sleeve 85.

Note that the present invention is not limited to the embodiment described above and various modification and alternations are possible and such modification and alternations also fall within the technical scope of the present invention.

What is claimed is:

1. An ultrasound endoscope comprising:
   an ultrasound transducer configured to transmit and/or receive ultrasound;
   a first drive wiring having a first portion and a second portion extending away from the first portion of the first drive wiring;
   a main circuit board comprising:
      a board material; and
      a first main circuit pattern provided on the board material, wherein the first main circuit pattern electrically connects the ultrasound transducer and the first portion of the first drive wiring;
   a first flexible sheet material attached to the main circuit board, the first flexible sheet material comprising:
      a first protection portion arranged to extend away from the main circuit board and to cover the first portion of the first drive wiring; and
      a first wrapping portion arranged to extend away from the first protection portion and to cover the second portion of the first drive wiring; and
   a housing comprising:
      a main circuit board housing portion configured to house the main circuit board, the first portion of the first drive wiring and the first protection portion of the first flexible sheet material; and
      a tubular drive wiring insertion portion extending away from the main circuit board housing portion, wherein the tubular drive wiring insertion portion is configured to house the first wrapping portion of the first flexible sheet material and the second portion of the first drive wiring.

2. The ultrasound endoscope according to claim 1, further comprising:
   a first flexible circuit pattern provided on the first flexible sheet material, wherein the first flexible circuit pattern electrically connects the ultrasound transducer and the first portion of the first drive wiring via the first main circuit pattern, wherein the first flexible circuit pattern comprises:
      a first flexible circuit pattern inner portion arranged on a first surface of the first flexible sheet material, wherein the first flexible circuit pattern inner portion is mechanically and electrically connected to the first main circuit pattern; and
      a first flexible circuit pattern outer portion arranged on a second surface of the first flexible sheet material, wherein the first flexible circuit pattern outer portion is mechanically and electrically connected to the first portion of the first drive wiring,
      wherein the first flexible circuit pattern inner portion is electrically connected to the first flexible circuit pattern outer portion, and
   wherein the first protection portion of the first flexible sheet material is arranged to cover the first flexible circuit pattern outer portion.

3. The ultrasound endoscope according to claim 1,
   wherein the ultrasound endoscope further comprises a second drive wiring having a third portion and a fourth portion extending away from the third portion of the second drive wiring;
   wherein the first main circuit pattern is arranged on a first surface of the board material,
   wherein the main circuit board further comprises a second main circuit pattern arranged on a second surface of the board material, wherein the second main circuit pattern electrically connects the ultrasound transducer and the third portion of the second drive wiring;
   wherein the first flexible sheet material is attached to the first surface of the board material; and
   wherein the ultrasound endoscope further comprises a second flexible sheet material attached to the second surface of the board material, the second flexible sheet material comprising a second protection portion arranged to extend away from the main circuit board and to cover the third portion of the second drive wiring.

4. The ultrasound endoscope according to claim 3, further comprising:
   a second flexible circuit pattern provided on the second flexible sheet material, wherein the second flexible circuit pattern electrically connects the ultrasound transducer and the third portion of the second drive wiring via the second main circuit pattern, wherein the second flexible circuit pattern comprises:
      a second flexible circuit pattern inner portion arranged on a first surface of the second flexible sheet material, wherein the second flexible circuit pattern inner portion is mechanically and electrically connected to the second main circuit pattern; and
      a second flexible circuit pattern outer portion arranged on a second surface of the second flexible sheet material, wherein the second flexible circuit pattern outer portion is mechanically and electrically connected to the third portion of the second drive wiring,
      wherein the second flexible circuit pattern inner portion is electrically connected to the second flexible circuit pattern outer portion, and
   wherein the second protection portion of the second flexible sheet material is arranged to cover the second flexible circuit pattern outer portion.

5. The ultrasound endoscope according to claim 3, wherein the first wrapping portion of the first flexible sheet material is arranged to extend away from the first protection portion and to cover the second portion of the first drive wiring and the fourth portion of the second drive wiring.

6. The ultrasound endoscope according to claim 3, wherein the second flexible sheet material further comprises a second wrapping portion arranged to extend away from the second protection portion and to cover the fourth portion of the second drive wiring.

7. The ultrasound endoscope according to claim 2,
wherein the ultrasound transducer, the first drive wiring, the main circuit board, the first flexible sheet material, the housing, and the first flexible circuit pattern form parts of an elongated insertion portion having a distal end and a proximal end that define an insertion axis,
wherein the ultrasound transducer comprises a plurality of ultrasound transducer elements configured to transmit and/or receive ultrasound, and
wherein each of the plurality of ultrasound transducer elements are arranged to transmit and/or receive ultrasound along one or more axes that intersect the insertion axis.

8. The ultrasound endoscope according to claim 7, further comprising a connection wire mechanically and electrically connecting at least one of the plurality of ultrasound transducer elements to the first main circuit pattern of the main circuit board,
wherein the first driving wire is mechanically and electrically connected to the first flexible circuit pattern outer portion, and arranged in the main circuit board housing portion and tubular drive wiring insertion portion to be substantially parallel to the insertion axis,
wherein the connection wire extends from the main circuit board towards the ultrasound transducer along an axis that intersects the insertion axis, and
wherein the first main circuit pattern and first flexible circuit pattern mechanically and electrically connect the connection wire and the first portion of the first drive wiring.

* * * * *